United States Patent [19]

Biller et al.

[11] Patent Number: 4,843,082
[45] Date of Patent: Jun. 27, 1989

[54] 1,2,3,4-TETRAHYDRO-8-QUINOLINOL DERIVATIVES AND ANTI-ALLERGIC USE THEREOF

[75] Inventors: Scott A. Biller, Ewing; Raj N. Misra, Hopewell, both of N.J.

[73] Assignee: E. R. Squibb & Sons, Inc., Princeton, N.J.

[21] Appl. No.: 859,981

[22] Filed: May 5, 1986

[51] Int. Cl.$^4$ .................... C07D 213/36; A61K 31/47
[52] U.S. Cl. ................................. 514/311; 546/165; 546/166; 546/179
[58] Field of Search ...................... 546/165, 166, 179; 514/311

[56] References Cited

U.S. PATENT DOCUMENTS

| | | | |
|---|---|---|---|
| 3,818,012 | 6/1974 | Nikles | 260/283 CN |
| 3,970,454 | 7/1976 | Gerbal | 96/29 D |
| 4,133,954 | 1/1979 | Sturm | 544/101 |
| 4,320,235 | 3/1982 | Merger et al. | 568/736 |
| 4,335,123 | 6/1982 | Grawinger et al. | 546/165 |
| 4,510,139 | 4/1985 | Bailey | 514/234 |

FOREIGN PATENT DOCUMENTS

| | | |
|---|---|---|
| 0065874 | 12/1982 | European Pat. Off. . |
| 0081321 | 6/1983 | European Pat. Off. . |
| 0083204 | 7/1983 | European Pat. Off. . |
| 0122518 | 10/1984 | European Pat. Off. . |

OTHER PUBLICATIONS

Chemical Abstracts, vol. 96, 159, 165m–"Spectrum of action of synthetic 8-oxyquinoline derivatives".
Indian Journal of Chemistry, vol. 12, pp. 252–257, 1974, "Condensed Heterotricycles*: Synthesis of Pyridine-annealed Dibenz[b,f][I,4]-oxazepines", Nagarajan et al.
Journal of American Chemical Society, vol. 89, pp. 3607–3612, 1967, "On Cobaloximes with Cobalt-Sulfur Bonds and Some Model Studies Related to Cobamide-Dependent Methyl-Group-Transfer Reactions", Schrauzer et al.

*Primary Examiner*—David B. Springer
*Attorney, Agent, or Firm*—Donald J. Barrack

[57] ABSTRACT

Leukotriene biosynthesis in macrophage cells is inhibited by compounds having the formula

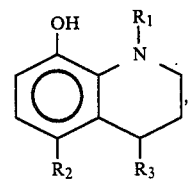

and pharmaceutically acceptable salts thereof, wherein
$R_1$ and $R_2$ are each hydrogen and $R_3$ is alkyl or arylalkyl;
$R_1$ and $R_3$ are each hydrogen and $R_2$ is arylmethyl or arylcarbonyl;
$R_1$ is methyl, $R_2$ is arylmethyl and $R_3$ is hydrogen; or
$R_1$ is alkyl of seven or more carbons or arylalkyl and $R_2$ and $R_3$ are each hydrogen.

15 Claims, No Drawings

1,2,3,4-TETRAHYDRO-8-QUINOLINOL DERIVATIVES AND ANTI-ALLERGIC USE THEREOF

BRIEF DESCRIPTION OF THE INVENTION

Leukotriene biosynthesis in macrophage cells is inhibited by 1,2,3,4-tetrahydro-8-quinolinol derivatives having the formula

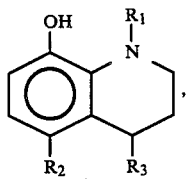

and the pharmaceutically acceptable salts thereof. In formula I, and throughout the specification, the symbols are as defined below.

$R_1$ and $R_2$ are each hydrogen and $R_3$ is alkyl or arylalkyl;

$R_1$ and $R_3$ are each hydrogen and $R_2$ is arylmethyl or arylcarbonyl;

$R_1$ is methyl, $R_2$ is arylmethyl and $R_3$ is hydrogen; or $R_1$ is alkyl of seven or more carbons or arylalkyl and $R_2$ and $R_3$ are each hydrogen.

Listed below are definitions of terms used to describe the compounds of this invention. These definitions apply to the terms as they are used throughout the specification (unless they are otherwise limited in specific instances) either individually or as part of a larger group.

The term "aryl" refers to phenyl and substituted phenyl. Preferred aryl groups are phenyl and phenyl substituted with 1, 2 or 3 alkyl of 1 to 4 carbons, alkoxy of 1 to 4 carbons, halogen or hydroxy groups.

The term "alkyl" refers to both straight and branched chain groups. Those groups having 1 to 12 carbons are preferred.

The term "halogen" refers to fluorine, chlorine, bromine and iodine.

Detailed Description of the Invention

The compounds of formula I, and the pharmaceutically acceptable salts thereof, inhibit leukotriene formation in macrophages (Samuelsson, B., Science, Vol. 220, p. 568–575 (1983)). Allergy of a reagin or non-reagin nature can be treated in mammals (e.g., humans) by the administration of a compound of this invention. Asthma is exemplary of the allergies that can be treated by the compounds of this invention. Any allergy where leukotrienes are involved as pharmacological mediators of anaphylaxis can also be treated with the compounds of this invention—allergic rhinitis, food allergy and urticaria are additional examples.

The dosage of a compound of this invention needed to treat an allergic condition will, of course, vary with the severity of the condition and the potency of the compound. The compounds can be administered orally or parenterally to mammals in need thereof, within a daily dosage range of about 1 to 100 milligrams of compound per kilogram of animal body weight (mg/kg), preferably about 1 to 50 mg/kg and especially about 2 to 25 mg/kg.

The compounds of this invention wherein $R_1$ and $R_2$ are each hydrogen and $R_3$ is alkyl or arylalkyl can be prepared by first reacting 2-aminophenol with methyl vinyl ketone

in the presence of a mineral oil at elevated temperature to yield 4-methyl-8-quinolinol.

Activation of 4-methyl-8-quinolinol, e.g., by treatment with lithium diisopropylamide, followed by reaction with an appropriate alkylating agent yields a compound having the formula

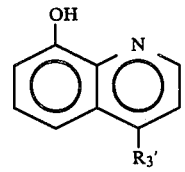

wherein $R_3'$ is alkyl or arylalkyl.

Catalytic hydrogenation of a compound of formula II using, for example, platinum oxide as the catalyst, yields the corresponding product having the formula

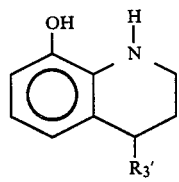

The compounds of this invention wherein $R_1$ and $R_3$ are each hydrogen and $R_2$ is arylmethyl or arylcarbonyl can be prepared by first acylating 8-hydroxyquinoline with the appropriate arylcarbonyl halide. The reaction proceeds most readily in the presence of a catalyst such as aluminum trichloride, and yields a compound having the formula

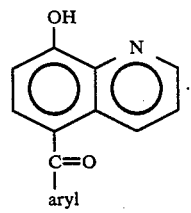

Treatment of a compound of formula IV with hydrazine in the presence of base (e.g., sodium hydroxide) and with heating yields the corresponding compound having the formula

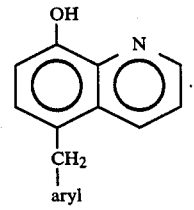

Catalytic hydrogenation of a compound of formula IV or V using, for example, platinum oxide as the catalyst, yields the corresponding product having the formula

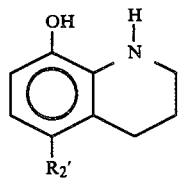

wherein $R_2'$ is arylmethyl or arylcarbonyl.

The compounds of this invention wherein $R_1$ is methyl, $R_2$ is arylmethyl and $R_3$ is hydrogen can be prepared by reacting a compound of formula VI, wherein $R_2'$ is arylmethyl, with formaldehyde and catalytically hydrogenating the resulting intermediate using, for example, a palladium on charcoal catalyst, to obtain the corresponding product having the formula

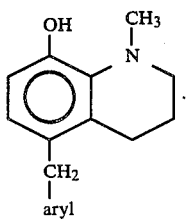

The compounds of this invention wherein $R_1$ is alkyl of seven or more carbons or arylalkyl and $R_2$ and $R_3$ are each hydrogen can be prepared by first catalytically hydrogenating 8-hydroxyquinoline (using, for example, platinum oxide) to obtain 1,2,3,4-tetrahydro-8-quinolinol. The partially hydrogenated compound can be reacted with an appropriate acylating agent (e.g., an acyl chloride) and subsequently chemically reduced (using, for example, borane) to obtain the corresponding product having the formula

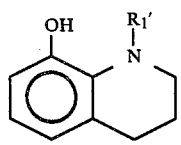

wherein $R_1'$ is alkyl of seven or more carbons or arylalkyl. Alternatively, 1,2,3,4-tetrahydro-8-quinolinol can be alkylated with the appropriate alkyl or arylalkyl halide ($R_1'$-halolgen) in the presence of sodium bicarbonate and hexamethylphosphoramide to obtain the corresponding product of formula VIII.

The compounds of formula I form acid-addition salts with a variety of inorganic and organic acids. The pharmaceutically acceptable salts include, for example, the hydrohalides (e.g., hydrochloride, hydrobromide, etc.), sulfate, phosphate, nitrate, arylsulfonates, (e.g., camphorsulfonate, benzenesulfonate, toluenesulfonate, etc.), citrate, ascorbate, maleate, fumarate, pamoate, acetate, tartrate, salicylate and the like. It is frequently convenient to isolate the compound by forming the acid salt and precipitating in a medium in which it is insoluble.

The following examples are specific embodiments of this invention.

EXAMPLE 1

4-Decyl-1,2,3,4-tetrahydro-8-quinolinol, monohydrochloride (A) 4-Methyl-8-quinolinol A solution of 100 ml of concentrated hydrochloric acid, 27.3 g (250 mmol) of 2-aminophenol and 41 ml (500 mmol, 2 eq.) of methyl vinyl ketone was heated to 110°–120° C. for 18 hours. The reaction was cooled, poured onto crushed ice, brought to pH 7 using 10N sodium hydroxide and extracted with ethyl acetate. The organic layers were washed with water, brine, dried (magnesium sulfate) and concentrated in vacuo. Purification by flash chromatography (silica gel, 1:2 ethyl acetate/petroleum ether) and crystallization (ethyl acetate) gave 5.3 g of the title compound as a light yellow solid: melting point 135°–136° C.

(B) 4-Decyl-8-quinolinol 1 A solution of 0.90 ml (6.3 mmol, 3.3 eq.) of diisopropylamine in 10 ml of dry tetrahydrofuran was cooled to −78° C. and 2.4 ml (5.7 mmol, 3 eq.) of 2.4M n-butyl lithium in hexane was added. The reaction was warmed to 0° C., stirred for 15 minutes and 0.30 g (1.9 mmol) of 4-methyl-8-quinolinol in 10 ml of dry tetrahydrofuran was added. The temperature was maintained at 0° C. for 24 hours, then the solution was warmed to room temperature and 3.0 ml (15 mmol, 8 eq.) of 1-bromononane was added. After stirring for one hour at room temperature, water was added and the reaction mixture was extracted with ether. The organic layers were washed with saturated ammonium chloride, brine, dried (magnesium sulfate) and concentrated in vacuo. Flash chromatography (silica gel, 1:9 ethyl acetate:petroleum ether) and subsequent recrystallization (methanol) gave 0.23 g of the title compound as pale green crystals: melting point 67°–68° C.

(C) 4-Decyl-1,2,3,4-tetrahydro-8-quinolinol, monohydrochloride

A sample of 138 mg (0.484 mmol) of 4-decyl-8-quinolinol partially dissolved in 10 ml of 7:3 methanol:2-propanol was bubbled with argon, 50 mg of platinum oxide was added and the mixture was hydrogenated on a Parr apparatus at 47 PSI for three hours. To aid dissolution, 0.6 ml of 1M hydrochloric acid was added, as well as an additional 50 mg of platinum oxide, and hydrogenation was continued at 42 PSI for another 3.5 hours. The suspension was filtered through a polycarbonate membrane. (0.4 μM pore size) and the filtrate was evaporated. The residue was partitioned between dichloromethane and saturated sodium bicarbonate, and the organic layer was dried (magnesium sulfate) and evaporated to give 139 mg of an oil. The crude material was flash chromatographed on 15 g of silica gel, eluted with 25:75 ethyl acetate:hexane to provide 42 mg of the free base. The hydrochloride salt was prepared with gaseous hydrogen chloride in ether to afford 46.9 mg of a greyish solid: melting point 159°–163° C. (softens 148°–159° C).

Analysis Calc'd. for $C_{19}H_{32}ClNO$: C, 70.02; H, 9.80; N, 4.30; Cl, 10.88; Found: C, 70.05; H, 9.94; N, 4.20; Cl, 10.87.

EXAMPLE 2

4-Heptyl-1,2,3,4-tetrahydro-8-quinolinol, hydrochloride

(A) 4-Heptyl-8-quinolinol

To a solution of 1.10 ml (7.88 mmol) of diisopropylamine in 20 ml of tetrahydrofuran at 0° C. under argon was added 4.1 ml (6.23 mmol) of 1.52M n-butyl lithium in hexanes dropwise. To the lithium diisopropylamide solution was added 502.0 mg (3.15 mmol) of 4-methyl-8-quinolinol (see example 1A) in 10 ml of tetrahydrofuran over 15 minutes at 0° C. The dark solution, which contained some insoluble material, was allowed to stir for five hours at 0° C., cooled to −78° C. and 0.46 ml (3.31 mmol) of 1-bromohexane was added. After 30 minutes at −78° C., the reaction was allowed to warm gradually from −30° C. to room temperature over 1.5 hours. The solution was allowed to stir for 45 minutes at room temperature, quenched with pH 6.5 phosphate buffer and extracted with ether. The ether extract was washed with water and brine, dried (magnesium sulfate) and evaporated to afford 757 mg of a yellow-brown solid. This material was dissolved in hot hexane, filtered to remove an insoluble residue and the filtrate was evaporated. Recrystallization from heptane provided 511.7 mg of the title compound as yellow plates: melting point 92°-93.5° C.

(B) 4-Heptyl-1,2,3,4-tetrahydro-8-quinolinol, hydrochloride,

A solution of 535 mg (2.19 mmol) of 4-heptyl-8-quinolinol in 30 ml of 1:1 methanol:ethyl acetate was hydrogenated at 44 PSI for 90 hours over platinum oxide. The indicated amounts of catalyst were added at the following times: 130 mg, 0 hours; 120 mg, 18 hours; 137 mg, 42 hours. At this juncture, some starting material still remained, and the catalyst was considered to be poisoned. The suspension was filtered through Celite, the filtrate was evaporated and the residue was dissolved in 50 ml of 4:1 methanol:ethyl acetate. This solution was hydrogenated at 44 PSI over 224 mg of platinum oxide for 48 hours. The suspension was filtered through a 0.4 μM polyester membrane filter and evaporated to provide a dark oil. Partial purification was achieved by flash chromatography on 65 g of silica gel, eluted with 25:75 ether:petroleum ether to provide 274.3 mg of impure pale green oil which refused to crystallize. The hydrochloride salt was prepared with hydrogen chloride in dry ether, and the crude salt was recrystallized from dichloromethane:ether and dried at 56° C. under vacuum to yield 191.3 mg of the title compound as a white solid:melting point 181°-183° C.

Analysis Calc'd. for $C_{16}H_{26}ClNO$: C, 67.70; H, 9.23; N, 4.94; Cl, 12.49; Found: C, 67.85; H, 9.36; N, 4.90; Cl, 12.46.

EXAMPLE 3

1,2,3,4-Tetrahydro-4-(2-phenylethyl)-8-quinolinol

(A) 4-(2-Phenylethyl)-8-quinolinol

A solution of 0.60 ml (4.2 mmol, 2.2 eq.) of diisopropylamine in 10 ml of dry tetrahydrofuran was cooled to −78° C. and 1.6 ml (3.8 mmol, 2 eq.) of 2.4M n-butyl lithium in hexane was added dropwise. The reaction was warmed to 0° C., stirred for 15 minutes and 0.30 g (1.9 mmol) of 4-methyl-8-quinolinol (see Example 1A) in 10 ml of dry tetrahydrofuran was added. The temperature was maintained at 0° C. for 24 hours, then was cooled to −78° C. and 0.23 ml (1.9 mmol, 1 eq.) of benzyl bromide was added. The reaction was stirred at −78° C. for one hour then stirred at room temperature for one hour. Water was added and this was extracted with ether. The organic layers were washed with saturated ammonium chloride, brine, dried (magnesium sulfate) and concentrated in vacuo. Purification by flash chromatography (silica gel, 1:4 ethyl acetate:petroleum ether) and recrystallization (petroleum ether) gave 240 mg of the title compound as pale green crystals: melting point 102°-103° C.

(B) 1,2,3,4-Tetrahydro-4-(2-phenylethyl)-8-quinolinol

A solution of 159 mg (0.638 mmol) of 4-(2-phenylethyl)-8-quinolinol in 18 ml of 5:1 methanol:ethyl acetate was hydrogenated over platinum oxide at 42–46 PSI for 46 hours. The catalyst was added in the following amounts at the indicated times: 32 mg, t=0 hours; 50 mg, t=7 hours; 22 mg, t=22 hours. The suspension was filtered through Celite and the filtrate was evaporated. The residue was flash chromatographed twice on silica gel (column 1 eluted with 20:80 ethyl acetate:petroleum ether; column 2 eluted with 40:60 ether:petroleum ether) to provide 101.8 mg of a colorless oil, which was recrystallized from benzene:hexane. The crystals were collected and dried under vacuum to afford 67.1 mg of the title compound as a white solid:melting point 90.5°-92° C.

Analysis Calc'd. for $C_{17}H_{19}NO.0.20$ eq. benzene: C, 81.27; H, 7.57; N, 5.21; Found: C, 80.87; H, 7.75; N, 5.14.

EXAMPLE 4

1,2,3,4-Tetrahydro-5-(phenylmethyl)-8-quinolinol, hydrochloride

(A) 5-Benzoyl-8-quinolinol

A solution of 8.70 g (60 mmol) of 8-hydroxyquinoline in 67 ml of nitrobenzene at room temperature under nitrogen was treated with 7.45 ml (65 mmol, 1.1 eq.) of benzoyl chloride and 20.0 g (150 mmol, 2.5 eq.) of aluminum trichloride in portions. The resultant mixture was heated at 110° C. for 7.5 hours and allowed to cool to room temperature. Ice and 20 ml of 10% hydrochloric acid was added before storing at 4° C. overnight. After the nitrobenzene was removed by steam distillation, the hot aqueous solution remaining in the pot was quickly decanted from the black tar which had formed and was allowed to cool. The crystals were filtered off and washed with 10% hydrochloric acid until the filtrate was pale yellow to yield 6.60 g of the hydrochloride salt of the title compound. The salt was taken up in a mixture of 300 ml of ethyl acetate, 200 ml of water and 9.8 g (120 mmol) of sodium acetate and stirred for 0.5 hour. The layers were separated and the organic phase was dried over sodium sulfate and evaporated to give 5.85 g of crude solid. Recrystallization from hexane provided 4.02 g of the title compound as a yellow solid: melting point 115°-116° C.

(B) 5-(Phenylmethyl)-8-quinolinol

To a solution of 2.88 g (72 mmol, 5.5 eq.) of powdered sodium hydroxide and 6.55 ml (135 mmol, 10.3 eq.) of hydrazine monohydrate in 40 ml of ethylene glycol was added 3.08 g (13.1 mmol) of 5-benzoyl-8-quinolinol and the resultant mixture was heated at 120° C. for one hour. The reflux condenser was removed and heating was continued until the pot temperature had reached 195° C. The condenser was replaced and refluxing continued for an additional three hours. The solution was cooled, diluted with 120 ml of water and brought to pH 7 with 1M hydrochloric acid. After the addition of 100 ml of pH 6.5 1M phosphate buffer and 500 ml of ethyl acetate, the layers were separated. The organic phase was washed with 100 ml of pH 6.5 1M phosphate buffer, two 100 ml portions of water and 100 ml of brine, dried over sodium sulfate and evaporated to yield 3.64 g of a dark brown, viscous oil. Purification required flash chromatography on 200 g of silica, eluted with 5:95 methanol:dichloromethane followed by recrystallization from heptane to provide 2.14 g of yellow crystals:melting point 112°-113° C.

(C) 1,2,3,4-Tetrahydro-5-(phenylmethyl)-8-quinolinol

To a solution of 702.8 mg (2.99 mmol) of 5-(phenylmethyl)-8-quinolinol in 40 ml of methanol and 8 ml of ethyl acetate under nitrogen was added 200 mg of platinum oxide and the mixture was hydrogenated at 40 PSI for four hours. Filtration through a 0.4 µm polyester membrane filter followed by evaporation yielded 733.8 mg of a dark tan solid. Recrystallization from dichloromethane:hexane and then flash chromatography on 50 g of silica eluted with 3:7 ethyl acetate:petroleum ether provided 534.5 mg: melting point 135°-136° C.

(D) 1,2,3,4-Tetrahydro-5-(phenylmethyl)-8quinolinol, hydrochloride

A solution of 199.8 mg (0.83 mmol) of 1,2,3,4-tetrahydro-5-(phenylmethyl)-8-quinolinol in 2 ml of dichloromethane was treated with 1 ml of hydrogen chloride-saturated dichloromethane. The addition of 15 ml of hexane resulted in the precipitation of a yellow solid. Microanalysis indicated that this material contained approximately 10% of the free base of the starting material. This mixture was taken up in 1 ml of methanol and treated with 0.5 ml of hydrogen chloride-saturated methanol, then 2 ml of dichloromethane and 10 ml of hexane. Evaporation gave a pale yellow, waxy solid, which was triturated with 5 ml of dichloromethane and 5 ml of hexane. Filtration provided 147.6 mg of the title compound as a pale yellow solid:melting point 219°-221° C. (decomposition 190°-219° C.).

Analysis Calc'd. for $C_{16}H_{18}ClNO$: C, 69.68; H, 6.58; N, 5.08; Cl, 12.86; Found: C, 69.32; H, 6.57; N, 5.07; Cl, 13.08.

EXAMPLE 5

5-Benzoyl-1,2,3,4-tetrahydro-8-quinolinol, hydrochloride

A mixture of 501.8 mg (2.01 mmol) of 5-benzoyl-8-quinolinol (see Example 4A) and 60.0 mg of platinum oxide in 38 ml of methanol was stirred at room temperature under a hydrogen balloon for three hours. Filtration through a 0.4 µm polyester filter and evaporation yielded 533.8 mg of a yellow solid. Flash chromatography on 55 g of silica eluted with 2:98 methanol:dichloromethane resulting in the separation of 94.3 mg of 1,2,3,4-tetrahydro-5-[(hydroxy)(phenyl)methyl]-8-quinolinol from 400.8 mg of a mixture of the title compound containing a small amount of 5-(cyclohexylcarbonyl)-1,2,3,4-tetrahydro-8-quinolinol. The mixture containing the desired product was purified by four recrystallizations from 1) ether-hexane, 2) benzene-hexane, 3) dichloromethane-hexane, and 4) ether-hexane to obtain 228.2 mg of 5-benzoyl-1,2,3,4-tetrahydro-8-quinolinol as a light yellow solid.

A solution of 215.1 mg (0.85 mmol) of 5-benzoyl-1,2,3,4-tetrahydro-8-quinolinol in 5 ml of ether was treated with 3 ml of hydrogen chloride saturated ether. The fluffy white precipitate was filtered off and recrystallized from dichloromethane-methanol-hexane to obtain 130.8 mg of a white solid, dried at 56° C./0.1 mm of Hg; melting point 237°-239° C., dec.

Analysis Calc'd. for $C_{16}H_{16}ClNO_2$: C, 66.32; H, 5.57; N, 4.83; Cl, 12.24; Found: C, 66.24; H, 5.58; N, 4.84; Cl, 12.19.

EXAMPLE 6

1,2,3,4-Tetrahydro-1-methyl-5-(phenylmethyl)-8-quinolinol

A solution of 50.6 mg (0.21 mmol) of 1,2,3,4-tetrahydro-5-(phenylmethyl)-8-quinolinol (see Example 4C) in 1 ml of methanol was treated with 32 µl (0.42 mmol, 2.0 eq.) of 37% aqueous formaldehyde and 105 µl (0.105 mmol, 0.5 eq.) of a 1M acetic acid/methanol solution and stirred for 50 minutes at room temperature under argon. To this solution was added 10 mg of 10% palladium on charcoal and the mixture was stirred under a hydrogen balloon for 22 hours. Filtration through a 0.4 µm polyester membrane filter and evaporation gave an oil, which was taken up in dichloromethane, washed with sodium bicarbonate and brine, dried over sodium sulfate and evaporated to give 46.5 mg of crude product as a tan solid. This was combined with crude material obtained from a similar reaction on 82.8 mg of 1,2,3,4-tetrahydro-5-(phenylmethyl)-8-quinolinol for a total crude weight of 113.3 mg.

Purification by flash chromatography on 12 g of silica, eluted with 12.5:87.5 tetrahydrofuran: petroleum ether provided 81.3 mg of a white solid: melting point 128°-129° C.

Analysis Calc'd. for $C_{17}H_{19}NO$: C, 80.59; H, 7.56; N, 5.53; Found: C, 80.58; H, 7.72; N, 5.39.

EXAMPLE 7

1-Heptyl-1,2,3,4-tetrahydro-8-quinolinol (A) 1,2,3,4-Tetrahydro-8-quinolinol

A solution of 2.5 g (17.2 mmol) of 8-hydroxyquinoline in 50 ml of methanol was treated with 680 mg of platinum oxide and was hydrogenated in a Parr apparatus at 40 PSI until hydrogen absorption ceased. The suspension was filtered through Celite, the filtrate was evaporated and the residue was recrystallized from dichloromethane: hexane to provide 1.82 g of analytically pure, green tinged needles: melting point 117.5°-119° C.

A portion of this material was recrystallized once more from dichloromethane:hexane to provide a near-white solid: melting point 118°-119.5° C.

(B) 1,2,3,4-Tetrahydro-(1-oxo-1-heptyl)-8-quinolinol

To a stirred solution of 355 mg (2.38 mmol) of 1,2,3,4-tetrahydro-8-quinolinol in 6 ml of tetrahydrofuran at room temperature was added 1 ml (12.4 mmol) of pyridine followed by the dropwise addition of 0.38 ml (2.45 mmol) of heptanoyl chloride (mild exotherm). Much precipitate developed, so an additional 5 ml of tetrahydrofuran was added to facilitate stirring. After 5 hours, the reaction mixture was diluted with ether, washed with 10% hydrochloric acid (two portions), water and brine, dried and evaporated to afford 618 mg of a pale yellow oil. Flash chromatography on 70 g of silica gel, eluted with 15:85 ethyl acetate:petroleum ether gave 178.9 mg of the N,O-bisacylated material followed by 376.5 mg of the title compound as a colorless oil.

(C) 1-Heptyl-1,2,3,4-tetrahydro-8-quinolinol

To a stirred solution of 364.5 mg (1.39 mmol) of 1,2,3,4-tetrahydro-(1-oxo-1-heptyl)-8-quinolinol in 7 ml of tetrahydrofuran at 0° C. under argon was added 7 ml (7 mmol) of 1M borane in tetrahydrofuran over 10 minutes. The solution was allowed to warm to room temperature and then heated to reflux for 22 hours. The reaction was allowed to cool to 0° C., quenched with methanol and evaporated. The residue was dissolved in 5 ml of methanol, saturated with hydrogen chloride gas and then heated to reflux for two hours. The methanol was evaporated, the residue was dissolved in ether and the solution was washed with saturated sodium bicarbonate and brine. After drying (magnesium sulfate), the solvent was removed in vacuo to afford 312 mg of an oily solid. The crude material was flash chromatographed on 40 g of silica gel, packed in 4:98 and eluted with 8:92 ethyl acetate:petroleum ether to provide 180.0 mg of the title compound as a white solid:melting point 33°–34° C.

Analysis Calc'd. for $C_{16}H_{25}NO$: C, 77.68; H, 10.19; N, 5.66; Found: C, 77.66; H, 10.27; N, 5.44.

EXAMPLE 8

1-Decyl-1,2,3,4-tetrahydro-8-quinolinol, hydrochloride (A) 1-Decyl-1,2,3,4-tetrahydro-8-quinolinol A mixture of 499.2 mg (3.35 mmol) of 1,2,3,4-tetrahydro-8-quinolinol (see Example 7A), 425 mg (5.05 mmol, 1.5 eq.) of sodium bicarbonate, and 780 µl (3.69 mmol, 1.1 eq.) of 98% 1-bromodecane in 10 ml of hexamethylphosphoric triamide under argon was stirred for three hours at room temperature, followed by 44 hours at 50° C. The reaction was diluted with 80 ml of 1:1 ether:petroleum ether and the organic layer was washed with five 40 ml portions of water and 40 ml of brine, dried over sodium sulfate and evaporated to yield 1.04 g of a brown oil. Purification by flash chromatography on 110 g of silica, eluted with 5:95 ethyl acetate:petroleum ether afforded 624.4 mg of the title compound as a colorless oil.

(B) 1-Decyl-1,2,3,4-tetrahydro-8-quinolinol, hydrochloride

A solution of 575.9 mg (1.99 mmol) of 1-decyl-1,2,3,4-tetrahydro-8-quinolinol in 1 ml of ether was treated with 5 ml of hydrogen chloride-saturated ether to afford a soluble hydrochloride. Evaporation provided an oil which solidified upon standing to give 564.2 mg of a waxy, ivory-colored solid:melting point 82°–83° C.

Analysis Calc'd. for $C_{19}H_{32}ClNO$: C, 70.02; H, 9.90; N, 4.30; Cl, 10.88; Found: C, 69.91; H, 10.05; N, 4.22; Cl, 10.55.

EXAMPLE 9

1,2,3,4-Tetrahydro-1-(phenylmethyl)-8-quinolinol, hydrochloride

A mixture of 2.00 g (13.4 mmol) of 1,2,3,4-tetrahydro-8-quinolinol (see Example 7A), 1.69 g (20.0 mmol, 1.5 eq.) of finely powdered sodium bicarbonate and 1.75 ml (14.7 mmol, 1.1 eq.) of benzyl bromide in 40 ml of hexamethylphosphoramide was stirred for 24 hours at room temperature under argon. The following work-up was carried out under conditions of minimum air exposure. Solvents and solutions were bubbled with nitrogen prior to use. The reaction mixture was diluted with 300 ml of 1:1 ether:petroleum ether and washed with five 100 ml portions of water and 100 ml of brine, dried over sodium sulfate and evaporated to obtain a tan solid. The solid was immediately dissolved in 10 ml of methanol, treated with 10 ml of hydrogen chloride-saturated methanol and diluted with 200 ml of ether. The precipitate was filtered, washed with ether, and dried under vacuum for 20 hours to afford 3.19 g of the title compound as an ivory solid; melting point 192°–194° C. (decomposition from 175° C.). $^1H$ NMR indicated that this material contained 0.16 equivalents of methanol.

Analysis Calc'd. for $C_{16}H_{18}ClNO$: C, 69.94; H, 6.60; N, 5.10; Cl, 12.90; Found: C, 69.74; H, 6.68; N, 5.05; Cl, 12.88.

What is claimed is:

1. A compound having the formula

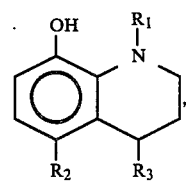

or a pharmaceutically acceptable salt thereof, wherein
$R_1$ and $R_2$ are each hydrogen and $R_3$ is alkyl or arylalkyl;
$R_1$ and $R_3$ are each hydrogen and $R_2$ is arylmethyl or arylcarbonyl;
$R_1$ is methyl, $R_2$ is arylmethyl and $R_3$ is hydrogen; or
$R_1$ is alkyl of seven or more carbons or arylalkyl and $R_2$ and $R_3$ are each hydrogen;
wherein the term "aryl" refers to phenyl or phenyl substituted with 1, 2 or 3 alkyl of one to four carbons, alkoxy of one to four carbons, halogen or hydroxy groups.

2. A compound in accordance with claim 1 wherein $R_1$ and $R_2$ are each hydrogen and $R_3$ is alkyl or arylalkyl.

3. A compound in accordance with claim 1 wherein $R_1$ and $R_3$ are each hydrogen and $R_2$ is arylmethyl or arylcarbonyl.

4. A compound in accordance with claim 1 wherein $R_1$ is methyl, $R_2$ is arylmethyl and $R_3$ is hydrogen.

5. A compound in accordance with claim 1 wherein $R_1$ is alkyl of seven or more carbons or arylalkyl and $R_2$ and $R_3$ are each hydrogen.

6. The compound in accordance with claim 1, 4-decyl-1,2,3,4-tetrahydro-8-quinolinol, or a pharmaceutically acceptable salt thereof.

7. The compound in accordance with claim 1, 4-heptyl-1,2,3,4-tetrahydro-8-quinolinol, or a pharmaceutically acceptable salt thereof.

8. The compound in accordance with claim 1, 1,2,3,4-tetrahydro-4-(2-phenylethyl)-8-quinolinol, or a pharmaceutically acceptable salt thereof.

9. The compound in accordance with claim 1, 1,2,3,4-tetrahydro-5-(phenylmethyl)-8-quinolinol, or a pharmaceutically acceptable salt thereof.

10. The compound in accordance with claim 1, 5-benzoyl-1,2,3,4-tetrahydro-8-quinolinol, or a pharmaceutically acceptable salt thereof.

11. The compound in accordance with claim 1, 1,2,3,4-tetrahydro-1-methyl-5-(phenylmethyl)-8quinolinol, or a pharmaceutically acceptable salt thereof.

12. The compound in accordance with claim 1, 1-heptyl-1,2,3,4-tetrahydro-8-quinolinol, or a pharmaceutically acceptable salt thereof.

13. The compound in accordance with claim 1, 1-decyl-1,2,3,4-tetrahydro-8-quinolinol, or a pharmaceutically acceptable salt thereof.

14. The compound in accordance with claim 1, 1,2,3,4-tetrahydro-1-(phenllmethyl)-8-quinolinol, or a pharmaceutically acceptable salt thereof.

15. A method of treating allergies in a mammalian species which comprises administering to a mammal in need thereof, an effective amount of a compound having the formula

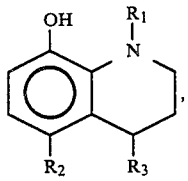

or a pharmaceutically acceptable salt thereof, wherein
$R_1$ and $R_2$ are each hydrogen and $R_3$ is alkyl or arylalkyl;
$R_1$ and $R_3$ are each hydrogen and $R_2$ is arylmethyl or arylcarbonyl;
$R_1$ is methyl, $R_2$ is arylmethyl and $R_3$ is hydrogen; or
$R_1$ is alkyl of seven or more carbons or arylalkyl and $R_2$ and $R_3$ are each hydrogen;
wherein the term "aryl" refers to phenyl or phenyl substituted with 1, 2 or 3 alkyl of one to four carbons, alkoxy of one to four carbons, halogen or hydroxy groups.

* * * * *